(12) United States Patent
Brown

(10) Patent No.: US 7,373,741 B1
(45) Date of Patent: May 20, 2008

(54) FOOT COVERING FOR MEDICAL USE

(76) Inventor: Cheryl F. Brown, 107 Grande Vista Way, Chelsea, AL (US) 35043

( * ) Notice: Subject to any disclaimer, the term of this patent is extended or adjusted under 35 U.S.C. 154(b) by 314 days.

(21) Appl. No.: 11/201,063

(22) Filed: Aug. 11, 2005

(51) Int. Cl.
*A43B 3/18* (2006.01)

(52) U.S. Cl. ........................................ 36/110; 36/7.1 R

(58) Field of Classification Search ................. 36/72 R, 36/7.5, 7.1 R, 77 R, 110, 11.5
See application file for complete search history.

(56) References Cited

U.S. PATENT DOCUMENTS

| | | | | |
|---|---|---|---|---|
| 2,081,655 A * | 5/1937 | Adams | ........................ | 36/140 |
| 2,193,943 A * | 3/1940 | Shea | ........................... | 36/11.5 |
| 2,973,590 A * | 3/1961 | Gaskill | ....................... | 36/72 R |
| 4,069,599 A * | 1/1978 | Alegria | ........................ | 36/7.2 |
| 4,107,857 A * | 8/1978 | Devlin | ........................ | 36/129 |
| 4,177,583 A * | 12/1979 | Chapman | .................... | 36/77 R |
| 4,237,628 A * | 12/1980 | Etancelin | .................... | 36/131 |
| 4,967,493 A * | 11/1990 | Mues | ......................... | 36/72 R |
| 5,410,821 A * | 5/1995 | Hilgendorf | .................. | 36/100 |
| 5,638,614 A * | 6/1997 | Hardy | ......................... | 36/113 |
| 5,711,092 A * | 1/1998 | Despres et al. | ............. | 36/72 R |
| 6,131,312 A * | 10/2000 | Hung | ......................... | 36/77 R |
| 6,272,771 B1 | 8/2001 | Rodi | | |
| 7,222,440 B2 * | 5/2007 | Dombowsky | ................ | 36/11.5 |
| 2001/0022039 A1 * | 9/2001 | Krajcir | ....................... | 36/72 R |
| 2003/0000107 A1 * | 1/2003 | Blackburn | .................... | 36/7.5 |
| 2003/0213149 A1 * | 11/2003 | Woods | ........................ | 36/110 |

* cited by examiner

*Primary Examiner*—Marie Patterson
(74) *Attorney, Agent, or Firm*—Crossley Patent Law; Mark Ashley Crossley

(57) ABSTRACT

A foot covering for medical use is described. The foot covering includes a sole that also has an upper insert tongue. The upper insert tongue covers approximately half of an individual's foot after the foot has been placed on the sole. Once a foot is placed within the foot covering, a pair of straps can be used to secure the upper insert tongue to the individual's foot so that the foot covering does not fall off while in use. The foot covering further includes a gripping tread to provide slip-resistance characteristics while in use.

5 Claims, 5 Drawing Sheets

FOOT COVERING FOR MEDICAL USE

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

The present invention concerns that of a new and improved foot covering for medical use.

DESCRIPTION OF THE PRIOR ART

U.S. Pat. No. 5,462,069, filed by Cohen, discloses a device to be used with a post-surgical boot for protecting the toes from injury and uncleaniness.

U.S. Pat. No. 4,177,583, filed by Chapman, discloses an orthopedic shoe with a domical forefoot protective guard to provide a safety zone for the distal portion of the foot.

U.S. Pat. No. 6,272,771, filed by Rodi, discloses a toe protector for orthopedic foot fixtures comprising a semi-rigid arcuate enclosure that is positioned over a patient's exposed toes extending from within a fabric foot fixture.

U.S. Pat. No. 5,609,570, filed by Lamont, discloses a medical boot that includes a two piece body unit.

U.S. Pat. No. 6,514,222, filed by Cook, discloses a protective apparatus for protecting an end of an appendage from physical contact after a surgical procedure.

SUMMARY OF THE INVENTION

The present invention concerns that of a new and improved foot covering for medical use. The foot covering includes a sole that also has an upper insert tongue. The upper insert tongue covers approximately half of an individual's foot after the foot has been placed on the sole. Once a foot is placed within the foot covering, a pair of straps can be used to secure the upper insert tongue to the individual's foot so that the foot covering does not fall off while in use. The foot covering further includes a gripping tread to provide slip-resistance characteristics while in use.

There has thus been outlined, rather broadly, the more important features of a foot covering for medical use that the detailed description thereof that follows may be better understood and in order that the present contribution to the art may be better appreciated.

There are, of course, additional features of the foot covering for medical use that will be described hereinafter and which will form the subject matter of the claims appended hereto.

In this respect, before explaining at least one embodiment of the foot covering for medical use in detail, it is to be understood that the foot covering for medical use is not limited in its application to the details of construction and to the arrangements of the components set forth in the following description or illustrated in the drawings. The foot covering for medical use is capable of other embodiments and being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present foot covering for medical use. It is important, therefore, that the claims be regarded as including such equivalent constructions insofar as they do not depart from the spirit and scope of the present invention.

It is therefore an object of the present invention to provide a foot covering for medical use which has all of the advantages of the prior art and none of the disadvantages.

It is another object of the present invention to provide a foot covering for medical use which may be easily and efficiently manufactured and marketed.

It is another object of the present invention to provide a foot covering for medical use which is of durable and reliable construction.

It is yet another object of the present invention to provide a foot covering for medical use which is economically affordable and available for relevant market segment of the purchasing public.

Other objects, features and advantages of the present invention will become more readily apparent from the following detailed description of the preferred embodiment when considered with the attached drawings and appended claims.

DESCRIPTION OF THE PREFERRED EMBODIMENT

Figure 1:
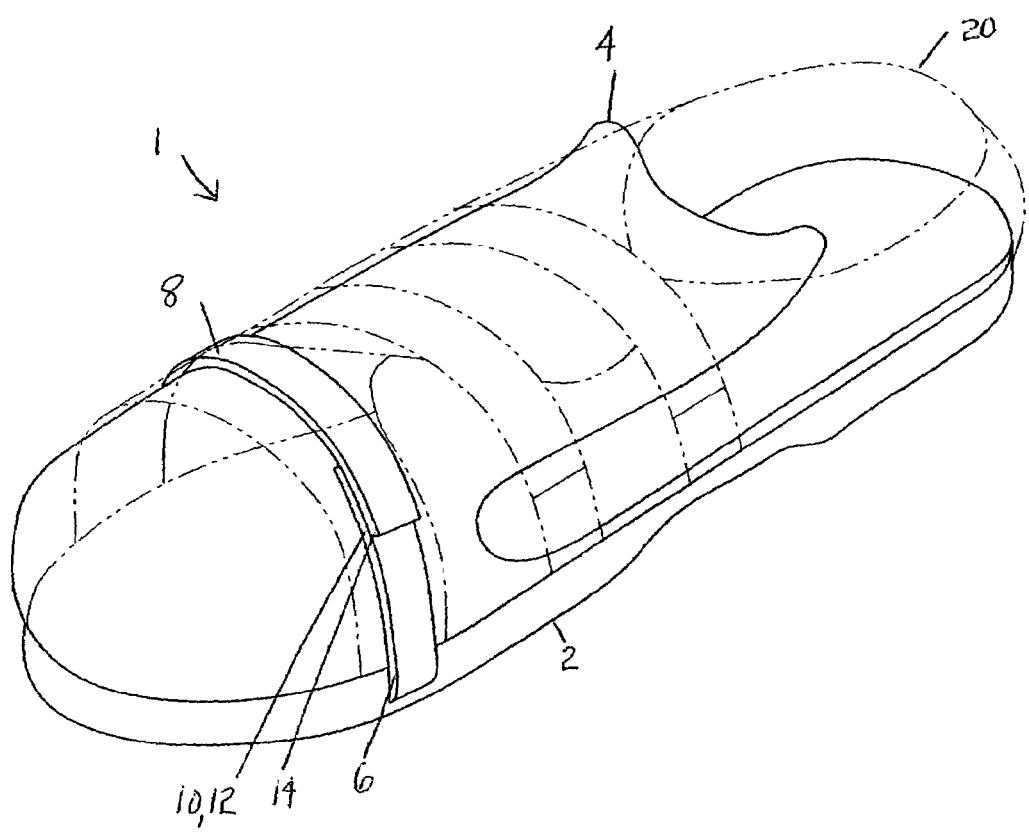
FIG. 1 shows a perspective view of the foot covering with a medical shoe inserted into the foot covering.
Figure 2:
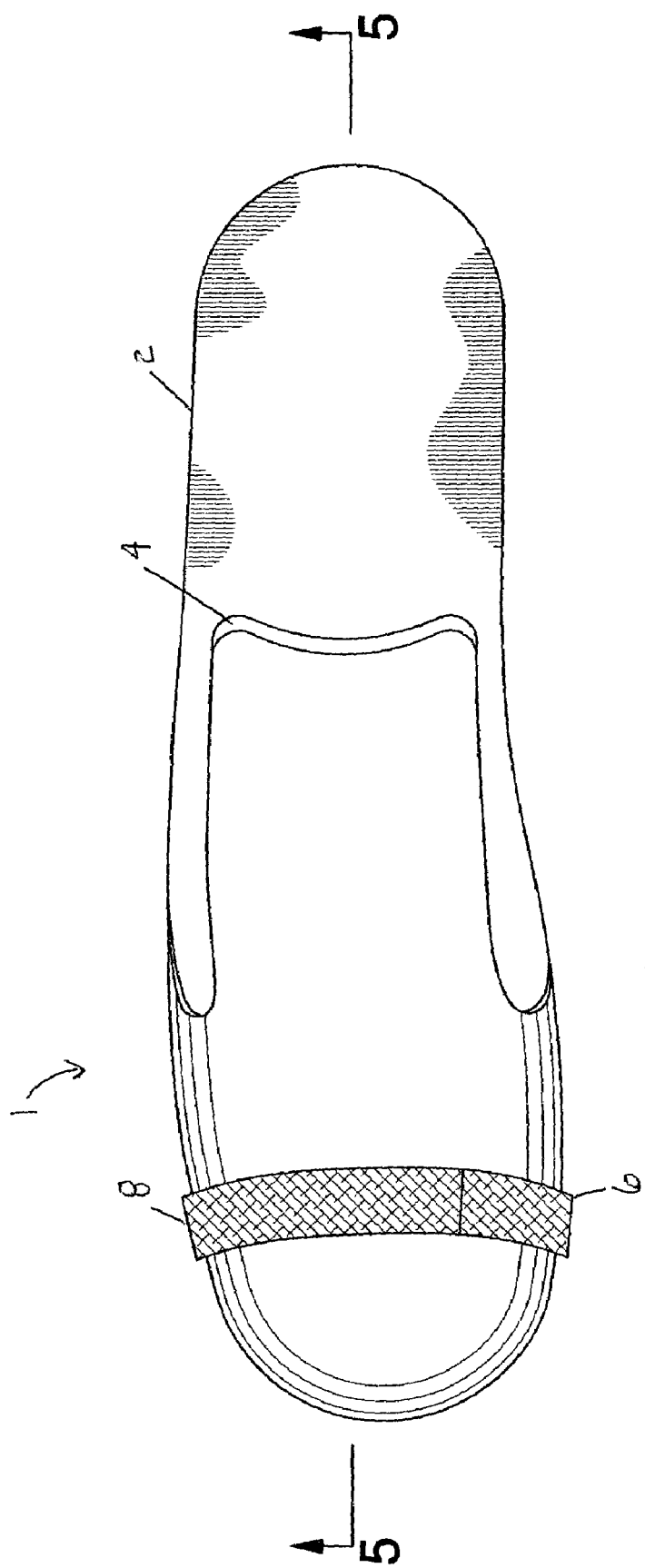
FIG. 2 shows a top view of the foot covering.
Figure 3:
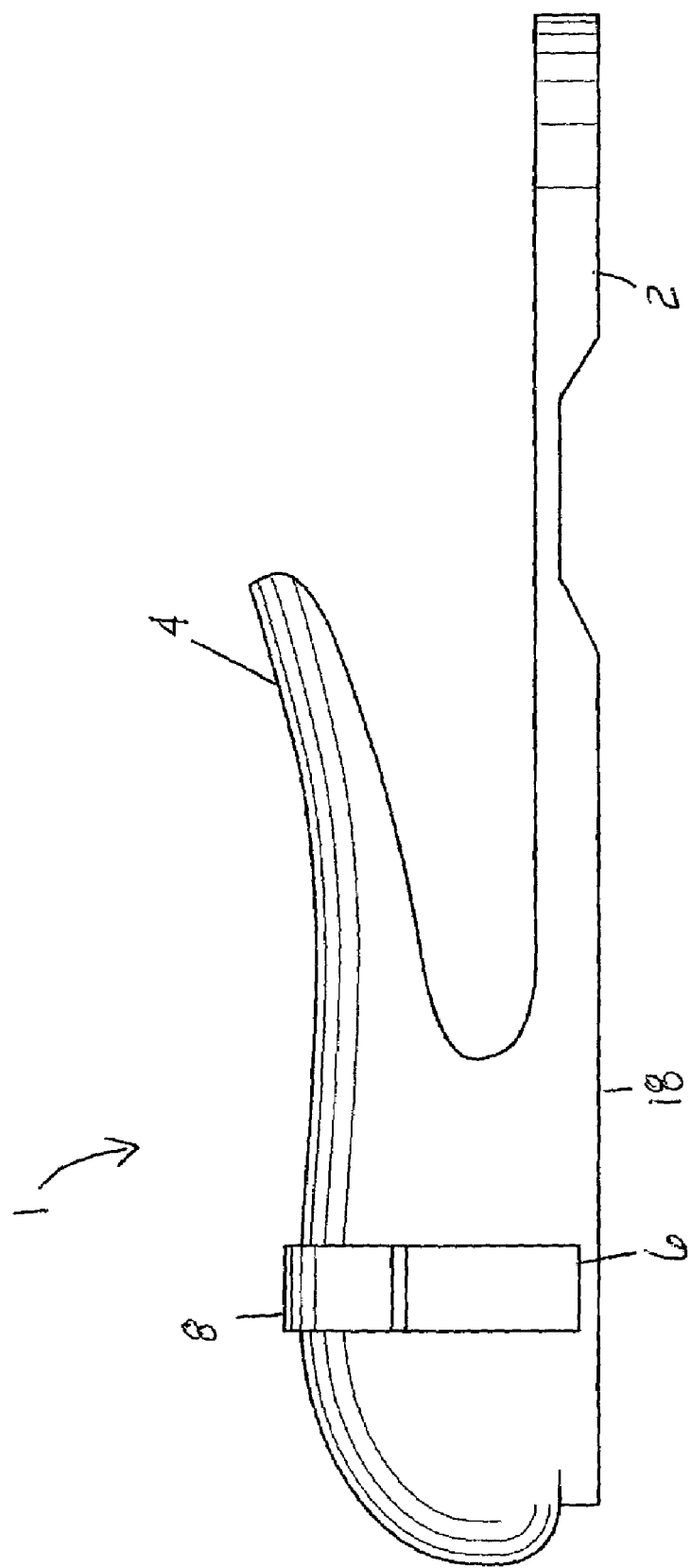
FIG. 3 shows a side view of the foot covering.
Figure 4:
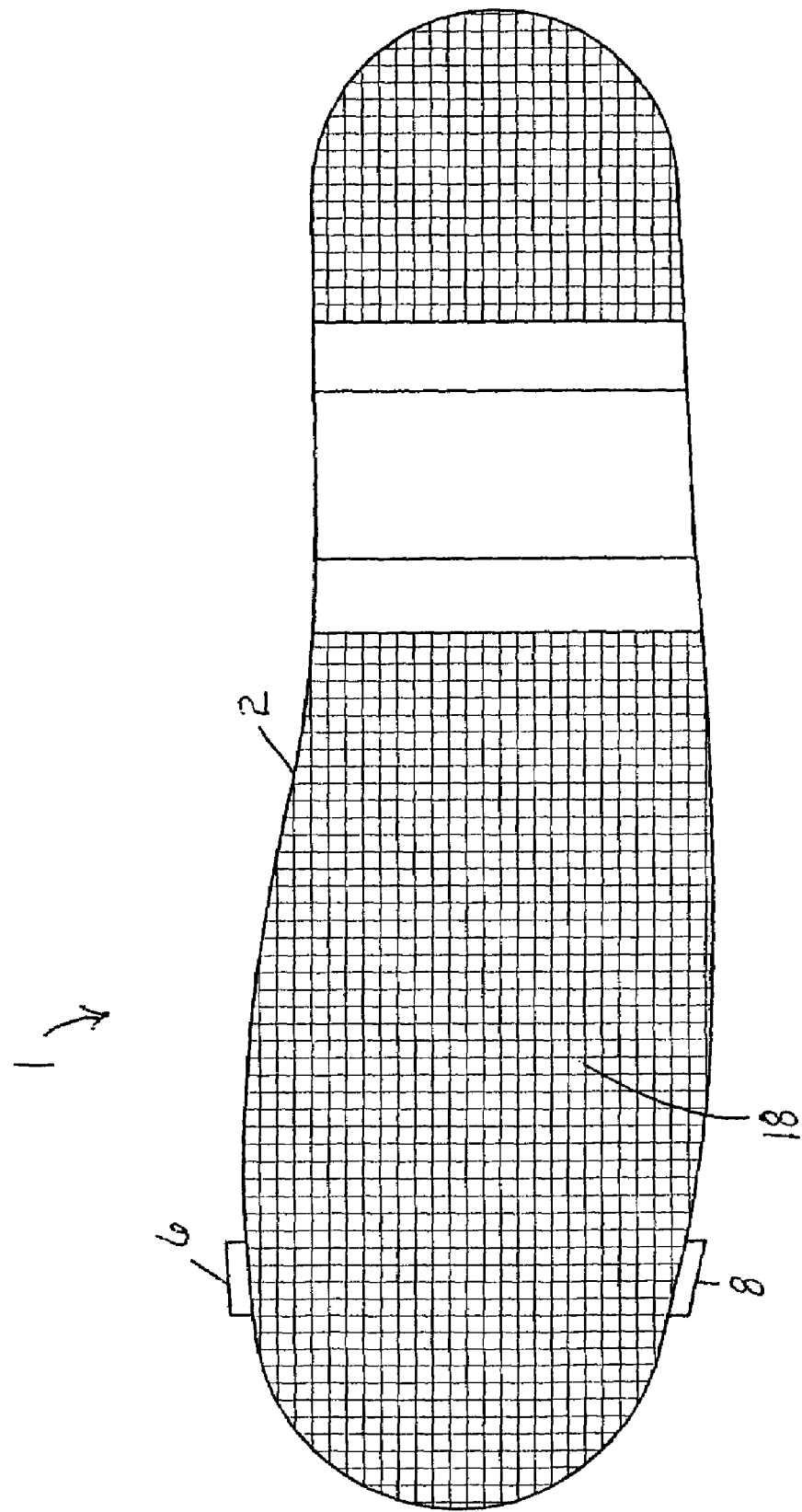
FIG. 4 shows a bottom view of the foot covering.
Figure 5:
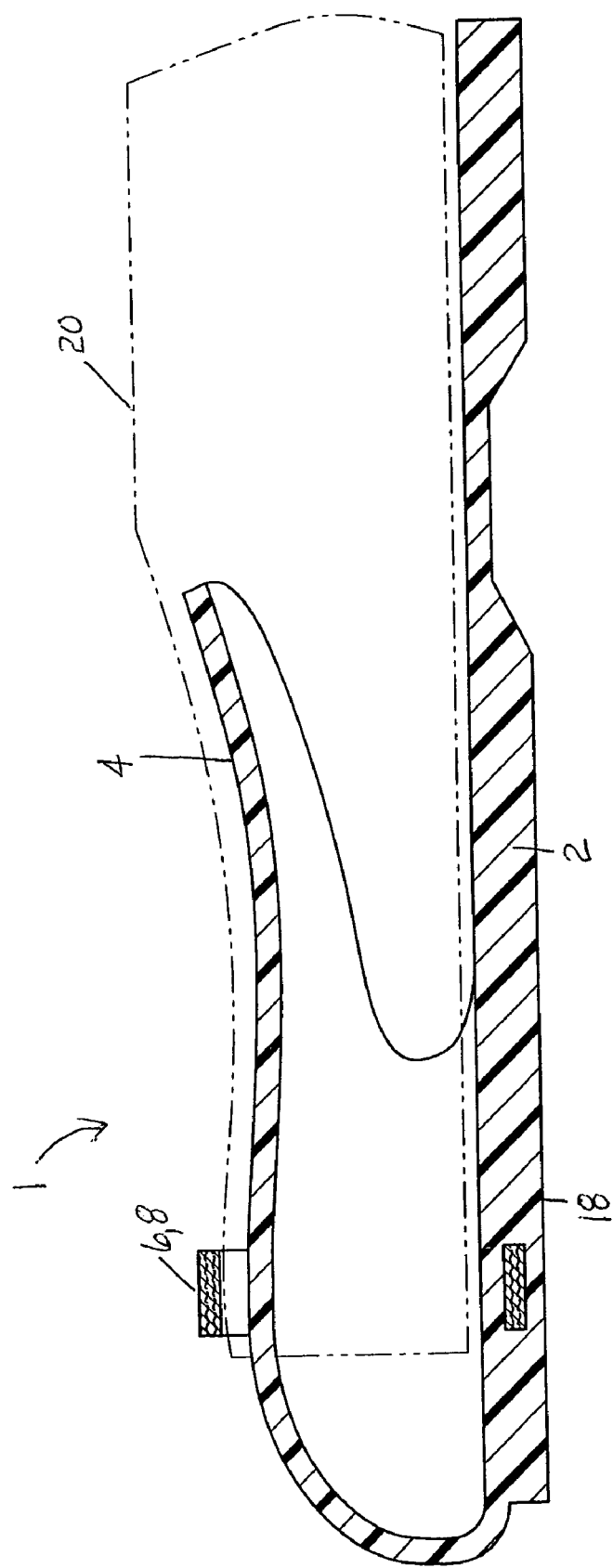
FIG. 5 shows a side cutaway view of the foot covering with a medical shoe inserted into the foot covering.

With reference now to the drawings, and in particular to FIGS. 1 through 5 thereof, a new foot covering for medical use embodying the principles and concepts of the present invention and generally designated by the reference numeral 1 will be described.

As best illustrated in FIGS. 1 through 5, the foot covering 1 comprises a sole 2 that has two surfaces, a top surface and a bottom surface. The sole 2 also has two ends, a front end and a rear end, and furthermore, has two sides, a left side and a right side.

An upper insert tongue 4 has two ends, a front end and a rear end. The front end of the upper insert tongue 4 is attached to the top surface of the sole 2 near the front end of the sole 2, while some of the upper insert tongue 4 is also attached to the left and right side of the sole 2 near the front end of the sole 2. The rear end of the upper insert tongue 4 is not attached to anything and culminates approximately halfway in between the front end and the rear end of the sole 2 while being located about two to three inches above the top surface of the sole 2.

Frequently, an individual must wear a medical shoe or medical boot. Usually, such a medical covering exposes an individual's toes. The foot covering 1 solves this problem by offering greater protection to the toes, concealing the area during the healing process, and offers a higher level of decorum for individuals who need to work during the recovery process.

Some of the drawings show a medical shoe 20 being inserted into the foot covering 1. The foot covering 1 essentially fits right over the medical shoe 20 just like a loafer or slipper with no backing would be attached to a bare foot.

Once the medical shoe 20 is placed within the foot covering 1, a pair of retaining straps 6 and 8 can be used to secure the medical shoe 20 within the foot covering 1. The retaining straps comprising a left retaining strap 6 and a right retaining strap 8. Left retaining strap 6 has two ends, a first end and a second end, and has two surfaces, an inner surface and an outer surface. The first end of the left retaining strap 6 is attached to the left side of the sole 2 near the front end of the sole 2. Right retaining strap 8 has two ends, a first end and a second end, and has two surfaces, an inner surface and an outer surface. The first end of the right retaining strap 8 is attached to the right side of the sole 2 near the front end of the sole 2.

The inner surface of the right retaining strap 8 near the second end of the right retaining strap 8 has a second patch 12, while the outer surface of the left retaining strap 6 near the first end of the left retaining strap 6 has a first patch 10. The first patch 10 has a first plurality of attachment objects 14, while the second patch 12 has a second plurality of attachment objects 16. Between the two pluralities of attachment objects, one of the pluralities of attachment objects comprises a plurality of loops, while the other plurality of attachment objects comprises a plurality of hooks.

An individual can secure the medical shoe 20 within the sole 2 of the foot covering 1 by placing the first patch 10 flush against the second patch 12 after the left retaining strap 8 and the right retaining strap 10 have been stretched tautly over the upper insert tongue 4. Once this occurs, the pressure generated by the straps 6 and 8 will assist in keeping the medical shoe 20 within the foot covering 1.

The foot covering 1 also has a gripping tread 18 on the bottom surface of the sole 2 of the foot covering 1. This gripping tread 18 provides additional support for an individual and prevents the individual from further injuring the foot and/or leg that is utilizing the medical shoe 20 for recovery purposes.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A foot covering for medical use in combination with a human foot and a medical covering enveloping the human foot, the foot covering comprising:
    (a) a sole having two surfaces, a top surface and a bottom surface, the sole also having two ends, a front end and a rear end, the sole also having two sides, a left side and a right side,
    (b) an upper insert tongue having two ends, a front end and a rear end, the front end of the upper insert tongue being attached to the top surface of the sole near the front end of the sole, the upper insert tongue also being attached to part of the left side and the right side of the sole near the front end of the sole, wherein the rear end of the tongue culminates about halfway between the front end and the rear end of the sole, further wherein the rear end of the tongue is located about two to three inches above the top surface of the sole,
    (c) means for securing the individual's foot and the medical covering on the foot once the foot and medical covering have been inserted into the sole and underneath the upper insert tongue, and
    (d) a gripping tread located on the bottom surface of the sole.

2. A foot covering for medical use according to claim 1 wherein the means for securing the individual's foot and the medical covering on the foot once the foot and medical covering have been inserted into the sole and underneath the upper insert tongue further comprises:
    (a) a left strap having two ends, a first end and a second end, the left strap also having two surfaces, an inner surface and an outer surface, the first end of the left strap being attached to the left side of the shoe near the front end of the sole,
    (b) a right strap having two ends, a first end and a second end, the right strap also having two surfaces, an inner surface and an outer surface, the first end of the right strap being attached to the right side of the shoe near the front end of the sole,
    (c) a first patch attached to the outer surface of the left retaining strap near the first end of the left retaining strap,
    (d) a second patch attached to the inner surface of the right retaining strap near the first end of the right retaining strap, and
    (e) means for removably securing the first patch to the second patch after tautly pulling the left retaining strap and the right retaining strap over the upper insert tongue.

3. A foot covering for medical use according to claim 2 wherein the means for removably securing the first patch to the second patch after tautly pulling the left retaining strap and the right retaining strap over the upper insert tongue further comprises:
    (a) a first plurality of attachment objects attached to the first patch,
    (b) a second plurality of attachment objects attached to the first patch,
    (c) wherein between the first plurality of attachment and the second plurality of attachment objects, one of the pluralities of attachment objects comprises a plurality of loops, while the other plurality of attachment objects comprises a plurality of hooks,
    (d) further wherein placing one of the patches into direct contact with the other patch will cause the two patches to become removably secured to one another.

4. A foot covering for medical use according to claim 3 wherein the medical covering located over the individual's foot comprises a medical boot.

5. A foot covering for medical use according to claim 3 wherein the medical covering located over the individual's foot comprises a medical shoe.

\* \* \* \* \*